United States Patent [19]  [11] 4,001,288
Gable et al.  [45] Jan. 4, 1977

[54] MAGNETIC ORGANO-IRON COMPOUNDS

[75] Inventors: Howard S. Gable, Kansas City; Glenn W. Kerr, Mission, both of Kans.

[73] Assignee: Howard S. Gable, Kansas City, Mo.

[22] Filed: Apr. 16, 1970

[21] Appl. No.: 29,008

Related U.S. Application Data

[63] Continuation-in-part of Ser. No. 487,565, Sept. 15, 1965.

[52] U.S. Cl. .................... 260/439 R; 252/62.51; 252/62.52; 252/62.53; 252/62.54; 252/62.56; 260/115; 260/117; 260/113; 260/123; 260/177; 260/270 R; 424/177; 424/295

[51] Int. Cl.$^2$ ........................................ C07F 15/02

[58] Field of Search ............... 260/439 R, 270, 115, 260/117, 123, 112; 424/295, 177; 252/62.56, 62.54, 62.51, 62.53, 62.52

[56] References Cited

UNITED STATES PATENTS

| | | | |
|---|---|---|---|
| 2,503,781 | 4/1950 | Van Meter et al. | 260/439 R |
| 2,849,334 | 8/1958 | Hart | 260/115 X |
| 3,200,136 | 8/1965 | Grossmith | 260/439 |
| 3,345,564 | 10/1967 | Makino et al. | 252/62.52 X |
| 3,480,555 | 11/1969 | Jackson et al. | 252/62.56 |

OTHER PUBLICATIONS

Hackh Chemical Dictionary McGraw–Hill Book Co., N.Y., N.Y., 4th edition (1969) p. 535.
Selwood Magnetochemistry Interscience Publishers Inc. New York, N.Y., 1956 (2nd edition) p. 309.
Elmore Phys. Rev. 54 (1938) pp. 309–310.

*Primary Examiner*—Arthur P. Demers
*Attorney, Agent, or Firm*—Leydig, Voit, Osann, Mayer & Holt, Ltd.

[57] ABSTRACT

An organo-iron compound or complex, having an X-ray diffraction pattern similar to that of magnetite and containing from 25 to 50 per cent or more iron, is water soluble and exhibits strongly ferromagnetic properties both as a solid and in aqueous solution. The compound is prepared by (1) precipitating a magnetite from an alkaline solution, optionally in the presence of a protein or protein degradation product, (2) optionally treating the precipitate with an oxidizing agent such as hydrogen peroxide, and (3) reacting the precipitate with a hydroxy-carboxylic acid. The resulting material is solubilized by treatment with a base.

21 Claims, 3 Drawing Figures

MAGNETIC ORGANO-IRON COMPOUNDS

CROSS-REFERENCE TO RELATED APPLICATION

This application is a continuation-in-part of our co-pending application Ser. No. 487,565 filed Sept. 15, 1965.

INTRODUCTION

This invention relates to a new class of iron compounds, or complexes, in which the iron is present in a magnetite-like crystalline structure and is in the ferromagnetic state while combined with organic groups. These compounds exhibit the property of visible mass magnetic attraction to even a small magnetic field. Organo-iron compounds containing iron in such a magnetic form have not been previously described. The fact that some of these compounds show a great solubility in water and in other solvents and possess these magnetic properties while in solution as magnetic responsive liquids is singularly unique and presents many possibilities for useful application.

SUMMARY OF INVENTION

According to the invention, water-soluble organo-iron compounds or complexes are produced by combining ferrous and ferric ions, in approximately the stoichiometric ratio of one molar part ferrous to two of ferric, in an alkaline solution of materials such as ammonia or alkaline hydroxides such as sodium or potassium hydroxides.

It appears that under these circumstances a magnetite structure is developed in situ in the precipitate, which is amenable to reactivity under appropriate conditions in a manner that is suggestive that this structure is acting as a reactive group per se. Through a variety of reactions it is possible to develope entire families of new chemical substances, all of which possess magnetic properties. Many of them possess properties relating to other groupings that have been attached, including such supplemental properties as solubility in various solvents.

Freshly precipitated magnetite, or, what is essentially the same thing, freshly precipitated magnetite which has been maintained in a moist state after precipitation, seems to possess a chemical reactivity that is not true of magnetite such as is found in natural minerals or magnetite which has been dried after preparation. This reactive magnetite may be utilized in various reaction without destroying its magnetic properties or altering the basic magnetite crystalline structure.

As a means of understanding the mechanism of these reactions which are herein considered it is helpful to utilize a background of the generally accepted theories related to magnetite structure. These are summarized by Wells (A. F. Wells, Structural Inorganic Chemistry, Third Edition, Oxford, pages 490–495 (1962)) and by Selwood (Pierce W. Selwood, Magnetochemistry, Second edition, Interscience, page 305 (1956)). Magnetite is properly considered a ferrite because it may be represented by the formula $MO \cdot Fe_2O_3$, in this case M = Fe II. Magnetite happens to have the "inverse spinel" structure. It is well known that in the spinels, the oxide ions form a face-centered cubic lattice and that the positive ions fill interstices between the oxygens. An examination of a model will show that there are two kinds of interstices, one of which has tetrahedral symmetry with four oxygen neighbors, the other octahedral symmetry with six oxygen neighbors. In normal spinels, the tetrahedral interstices are occupied by the divalent ions (M II), the octahedral by Fe III; but in inverse spinels the Fe III ions ocupy the tetrahedral holes and the divalent ions some of the octahedral spaces. Thus, magnetite has, for each Fe III in a tetrahedral hole, one Fe III and one Fe II in an octahedral hole. The crystallographic unit cell contains thirty-two close-packed oxygen atoms and twenty-four positive ions of which one third are Fe II and the remainder Fe III, or 8($Fe_2O_3 \cdot FeO$).

The $Fe_2O_3$ in the magnetite is $\gamma$-$Fe_2O_3$ and possesses magnetic properties. In the $\gamma$-$Fe_2O_3$ there are on the average only twenty-one and one-third Fe atoms per unit cell distributed at random among the eight tetrahedral and sixteen octahedral sites. Accordingly $\gamma$-$Fe_2O_3$ and $Fe_3O_4$ are easily interconvertible. Careful oxidation of $Fe_3O_4$ yields $\gamma$-$Fe_2O_3$ which is converted back to $Fe_3O_4$ by heating in vacuum at 250° C. Observations that the ferrous iron portion of the magnetite is not closely bound and that there are many variations in the amounts of ferrous iron in magnetites are due, at least in part, to the work of Welo and Baudisch (L.O. Welo and O. Baudisch, Phil. Mag. (7) 3, 396 (1927)).

When the freshly precipitated magnetite is oxidized in the cold with hydrogen peroxide this oxidizattion tends to oxidize the Fe II in the unit cell so that the oxidized magnetite may contain in the range of no more than one to three percent Fe II rather than one-third of the total iron as in the theoretical magnetite. As will be described below, the magnetite crystalline structure remains intact. Such an oxidized magnetite has a rather deep brownish color rather than the dark black color of unaltered magnetite.

If freshly precipitated magnetite or freshly precipitated magnetite which has been oxidized by hydrogen peroxide be reacted with aqueous solutions of hydroxy-carboxylic acids it is possible to effect a chemical combination between either the magnetite or the oxidized magnetite and the hydroxy-carboxylic acid, wherein the crystalline structure and the magnetic properties of the magnetite remain in the complex which is formed. It would appear therefore as if the magnetite was acting as an integral reactive ion in itself.

This unique reactivity is the basis for a new chemistry with respect to magnetic materials.

The hydroxy-carboxylic acids form a very broad class and all of the members of this class which are capable of combining with the magnetite to form an alkali-soluble complex are suitable for this application. It has been found that acids from the group of hydroxy-polycarboxylic acids such as citric acid, polyhydroxy-carboylic acid such as gluconic acid, or polyhydroxy-polycarboxylic acids such as tartaric acid are quite suitable, and that tartaric acid which is cheap and easily available is quite satisfactory and is the one employed in the discussions which follow. Certain other acids such as ascorbic acids may, however, be utilized. Some other hydroxy-carboxylic acids are listed in Beilstein's "Handbuch der Organischen Chemie", or Kirk-Othmer's "Encyclopedia of Chemical Technology", Second Edition (Interscience), in the section on "Acids, Carboxylic".

The product resulting from reaction with a hydroxy-carboxylic acid such as tartaric acid is insoluble in water, whilst some iron is solubilized by the tartaric acid and appears in the filtrates and washings. The former material, while insoluble in water, maintains the magnetic properties of the original magnetite. If the freshly precipitated magnetite is employed rather than the magnetite which has been oxidized with hydrogen peroxide, it is noticed that the reddish product is contaminated by a yellow-green polynuclear complex between iron and tartaric acid which does not possess the desired ferromagnetic properties, and is an impurity that may be avoided by the hydrogen peroxide oxidation procedure.

The complex formed between the magnetite and a hydroxycarboxylic acid such as tartaric acid contains reactive groups which will react with alkaline materials to form soluble products. Examples of such alkaline materials include ammonia, the alkali metal hydroxides and many organic bases such as lower alkyl amines, piperidine, the quaternary ammonium bases such as tetramethylammonium hydroxide, guanidine derivatives such as tetramethylguanidine and related materials. Quadrol, an ethylenediamine derivative is very satisfactory.

These soluble compounds formed as a result of the solubilizing reaction with bases may be precipitated from solution with dilute acid and then be resolubilized by a base and this procedure repeated many times, provided only that care be taken not to employ an acid strong enough to decompose the compound. These soluble compounds may be recovered from solution by evaporation to give a dry reddish-brown powder which can be resolubilized. During all of these steps the magnetic properties of the material remain, and X-ray diffraction studies give every indication that the basic magnetite structure is inherent in the compounds.

Beyond this it is possible to considerably broaden the confines of this class of magnetic compounds by the introduction of additional organic groupings into the molecule. One direction of this embraces the use of proteins or protein degradation (e.g. decomposition or modification) products, including polypeptides, peptides, amino acids and the like, that may themselves to some extent have been altered as the result of the hydrolysis, oxidation or other procedure that has released them from the protein.

It is to be noted that the introduction of such protein and protein degradation products is better effected when these products are present in the solution from which the magnetite is precipitated as they seem to undergo an in situ reaction during the magnetite formation.

In this very broad class of compounds the iron is always present in the magnetite structure as shown by X-ray diffraction analysis, albeit frequently showing a great deficiency of ferrous iron. The iron content of these compounds, as expressed as elemental iron, may compose over fifty percent of the weight of the compound. The number and molecular weights of the organic groups determine the lower limits of iron content.

It is frequently more desirable to prepare these new chemical compounds of iron wherein the molecular size is smaller than would result from the utilization of a complete protein molecule. A convenient procedure for the preparation of such derivatives rests in the degradation of a protein, such as gelatin, with an active agent such as hydrogen peroxide. It has been shown (Paul M. Gallop, Sam Seifter and Edward Meilman, "Some Observations on the Oxidation of Ichthyocol and Its Derived Gelatin", Recent Advances in Gelatin and Glue Research, pages 82–91, Pergamon Press (1958)), by sedimentaion patterns obtained in the analytical ultracentrifuge, that when gelatin is subjected to treatment with hydrogen peroxide it undergoes a continual decrease in molecular weight until only relatively small peptides of 10,000 molecular weight or less remain. More vigorous oxidation of the gelatin than attained in the conditions employed by Gallop and co-workers will result in the further degradation of the protein molecule and in the released peptides.

Such peptide-amino acid mixtures are easily prepared and serve as a satisfactory intermediate material for the preparation of these organo-iron compounds. Other agents may also be employed for protein modification. These include mineral acids such as hydrochloric or sulphuric acids, or alkalies such as sodium or potassium hydroxide in a range of concentrations and under various conditions of heat and pressure. It is also possible to utilize enzymes and the process of microorganism fermentation for the protein alteration. There are obvious advantages of economy in the use of proteins as a starting material over a procedure that would be based upon the employment of the various pure chemicals that might result from a protein degradation, unless there is a compelling requirement for a highly specific compound.

In these experiments, iron is introduced into the reaction through a carrier compound wherein the iron is present in the ferrous state, such as iron is present in ferrous chloride, which provides a convenient starting material.

Broadly speaking, the protein or the protein degradation products such as result from the hydrogen peroxide oxidation of gelatin, containing a specific amount of excess hydrogen peroxide, are brought into a chemical combination with ferrous chloride. The content of hydrogen peroxide is calculated to be sufficient to oxidize approximately two-thirds of the total iron to the ferric state. While it is possible to utilize a mixture of ferrous and ferric chlorides to obviate the necessity of oxidizing the greater portion of the iron present in the ferrous chloride to ferric iron by the use of hydrogen peroxide, this procedure generally results in the formation of organo-iron compounds containing a smaller amount of organic groupings than are usually desired for the finished compound. The hydrogen peroxide may well serve a dual role. Sufficient ammonium hydroxide is added to this combination to convert all of the chlorine originally present in the ferrous chloride into ammonium chloride and to leave a slightly alkaline reaction mixture. As a consequence of this reaction a ferrosic iron oxide is formed which is in chemical combination with organic components provided by the degradated protein. This compound appears in the form of a dark greenish-blue precipitate which gradually assumes a blackish color. The precipitate that first forms is only weakly magnetic, but the magnetic strength increases as it ages and darkens. This reaction is carried out at room temperature without the heating that is normally employed for the preparation of magnetite. The use of heat at this stage seems to interfere with some of the later processing, and there is some reduction in the organic portion of the finished compound.

This black magnetic compound (i.e. magnetite with protein or protein degradation products) is a polyfunctional material that will enter into reactions with both acids and bases. It is also capable of being transformed by other chemical reagents. Here again, it is advantageous to convert the black magnetic compound by hydrogen peroxide oxidation of ferrous iron to a dark brownish colored material in order to avoid side reactions which would produce undesirable contaminating products. This brown compound which retains protein residues and possesses magnetic properties can be separated from the supernatant liquid and perified by repeated washings with water. It is relatively stable, especially as a wet filter cake. This brown compound contains in the range of fifty percent elemental iron in combination with organic groups.

The brown material is further processed by reacting it with aqueous solutions of suitable hydroxy-carboxylic acids. This reaction with the organic acid is highly critical. Acids possessing a sufficiently high dissociation constant to serve in the formation of derivatives are also sufficiently powerful to badly damage the compound or even to completely destroy it by converting the iron to mixtures of nonferromagnetic salts of the organic acid. If, on the other hand, the reaction is not allowed to proceed to the proper stage, the resulting material will not possess the desired solubility and magnetic properties. The reaction is a function of variable factors which include the ratio of the oraganic acid to the brown magnetic compound, the concentration of the acid solution, the temperature at which the reaction is conducted and the duration of contact between the reactants. Various combinations of these variables may be utilized to produce a satisfactory product.

When tartaric acid is employed, the brown compound is gradually converted into one with a reddish hue which possesses strong magnetic properties. This red magnetic compound is separated from the acid solution and is washed free from water-soluble impurities. It is relatively stable, particularly as a wet filter cake. It has an iron content which may range from about twenty-five or twenty-seven to fifty percent or more on a dry basis. This wide span in iron content is an indication of the variability of this reaction in which chemical compounds are formed by gradations over a considerable area depending upon the extent of the reaction.

This red magnetic compound is a complex embodying the magnetite crystalline structure in an involvement with protein residues and organic acid. It possesses free acidic groups and may be converted into a water-soluble form by the preparation of a suitable salt. Salts may be formed with an alkali metal such as sodium or potassium, or with ammonium or some substituted ammonia or organic base utilized, providing it has a sufficiently high dissociation constant, $K_b$ to suitably react and to form a stable compound. Most organic bases with a $K_b$ in excess of about $1 \times 10^{-6}$ will react, however, other qualities than alkalinity are also involved in the reaction and influence the properties of the reaction product. Among the organic bases that will react under these conditions are the alkyl amines, in the lower members of the series, piperidine, the quaternary ammonium bases such as tetraethylammoniumhydroxide, quanidine derivatives, such as tetramethylguanidine and other related materials. Piperidine, tetramethylguanidine and Quadrol are quite satisfactory.

If an aqueous slurry is made of the wet filter cake of the red compound and this treated with the alkali, an immediate solution is effected of all but a trace of the material. Other solvents such as glycerin or ethylene glycol may also be used. This solution of the salt of the red magnetic compound is of a deep reddish-black color reminiscent of that of bromine when the solution is of even a moderate concentration. Weak solutions have a reddish-yellow coloration. The solution exhibits the phenomenon of mass magnetic attraction when it is brought in the proximity of even a small magnetic field.

The material as above described is a mixture of different organo-iron compounds covering a broad range of molecular compositions. For many applications it is unnecessary to resolve it into distinct chemical components.

The great solubility of these salts of the red magnetic compound is highly significant. Indeed, in some instances the water solubility is essentially infinite in that a completely homogenous system is formed without saturation equilibrium or numerical value for solubility. This solubility characteristic is in itself a proof that in constitution, the material is a macromolecule or a high polymer. (Arnold Weissberger: *Physical Methods of Organic Chemistry*, Volume I, Part 1, page 666, Interscience, New York (1959)).

It is also possible to effect transformations of either the brown or of the black magnetic material into other new chemical combinations by virtue of reactivity with basic substances (See Group B, Example No. 2, below). Such reactions are preferably conducted with organic bases. Generally speaking, almost any organic base may be utilized provided it has a dissociation constant, $K_b$ in excess of about $1 \times 10^{-6}$. This includes ammonia, the alkyl amines in the lower members of the series, piperidine, quaternary ammonium bases such as tetraethylammoniumhydroxide, guanidine derivatives such as tetramethylguanidine, and other related materials. Here, too, qualities other than alkalinity are involved and basic materials are not to be considered necessarily equivalent. Here, a completely stable material is more difficult to achieve than by the earlier procedure. In most of these cases, the reaction is not instantaneous and may well involve deep seated molecular changes. At any rate, it is only neccessary to allow either the black or brown material to stand in contact with the base or an aqueous solution of it to effect a reaction which usually results in a solubilization of the material. These solutions appear black in color except in great dilution when they assume a brownish tinge. These solutions exhibit the phenomenon of mass magnetic attraction when brought in the proximity of even a small magnetic field.

As has been indicated, the avenue for the preparation of these new organo-iron compounds stems from a precipitaiton preparation of ferrosic oxide (i. e. magnetite; one molar part ferrous to two of ferric ions) in the presence of alkaline materials and reaction with suitable reactive groups which enter into complex, apparently polynuclear, structures with the ferrosic oxide during its formation. These complex compounds between organic groups and the ferrosic oxide configuration have a general stability which is maintained through chemical reactions involving various segments of the organic portion of the molecule, and which may even alter the constitution of the spinelic structure itself. The ferrosic oxide configuration seems to serve as a nucleus around which various organic structures may be built.

The chemical reactions above described are obviously highly complex, involving as they do an entire series of chemical transformations utilizing some of the most complicated chemical structures as starting materials for elaboration into new and even more intricate combinations. Variations are possible over a wide range depending upon the specific operation procedure that is followed. It is not possible at this time to completely define the nature of the various stages of these transformations or to elucidate the chemical structures of the organo-iron compounds which result. As has been indicated, certain stages in the procedure are critical if a suitable soluble magnetic compound is desired; some conditions may be varied over a considerable range.

X-RAY DIFFRACTION

It has been established, by X-ray diffraction studies that the basic magnetite structure persists in all members of this family of compounds, but the exact nature of the linkages of the organic groupings is yet to be accurately elucidated.

Figure 3:
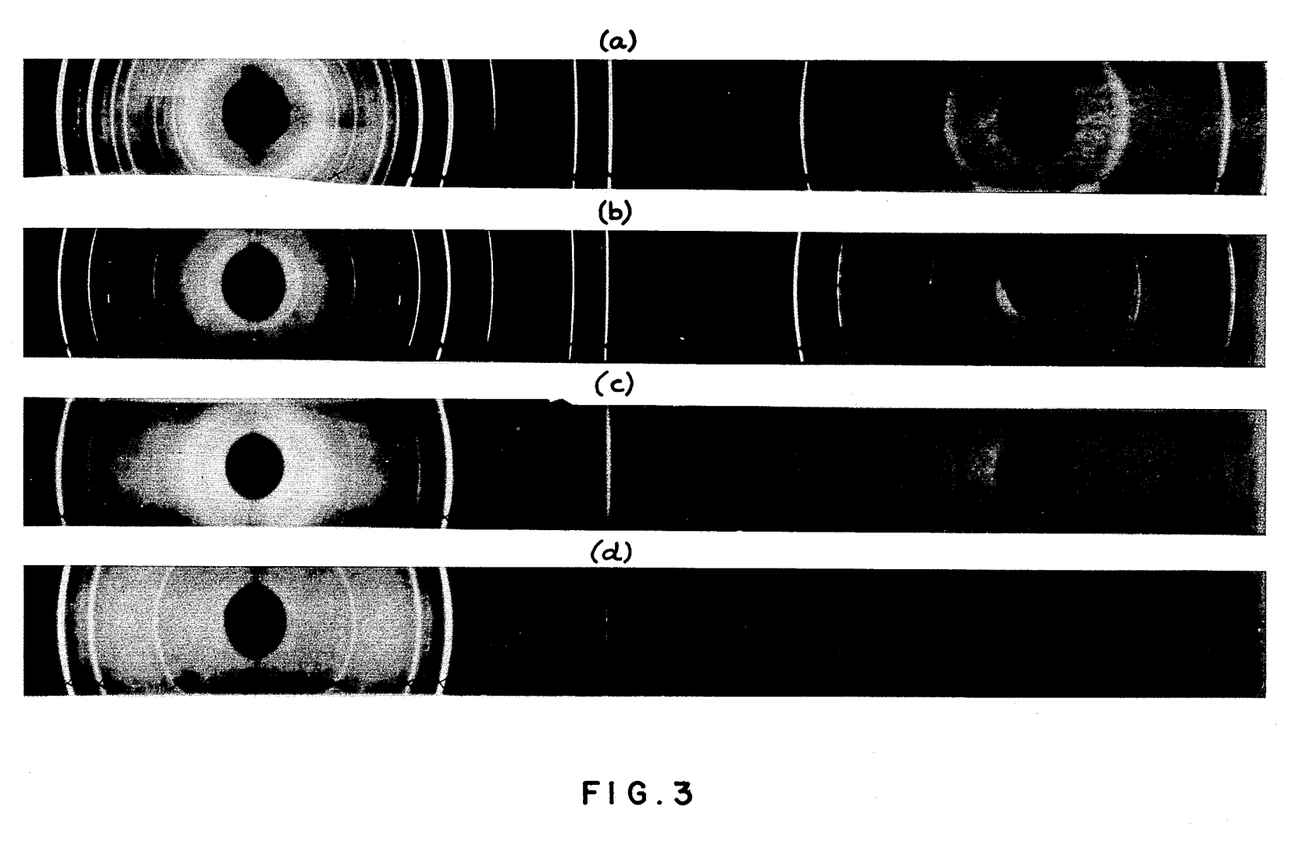
FIG. 3 shows X-ray diffraction patterns for (a) gamma $Fe_2O_3$, (b) technical magnetite, (c) freshly precipitated magnetite reacted with tartaric acid and Quadrol (i.e., 1, 1′, 1″, 1‴(ethylenedinitrilo-tetra-2-propanol), and (d) wet freshly precipitated magnetite.

X-ray diffraction patterns, taken with a filmstrip camera, are shown in FIG. 3. FIG. 3a is the pattern of mineral gamma ferric oxide; FIG. 3b is that of technical magnetite; FIG. 3c is that of a product according to the invention prepared by treating freshly precipitated magnetite with tartaric acid and then with Quadrol; and FIG. 3d is the pattern of a wet, freshly precipitated, magnetite without treatment.

Figure 1:
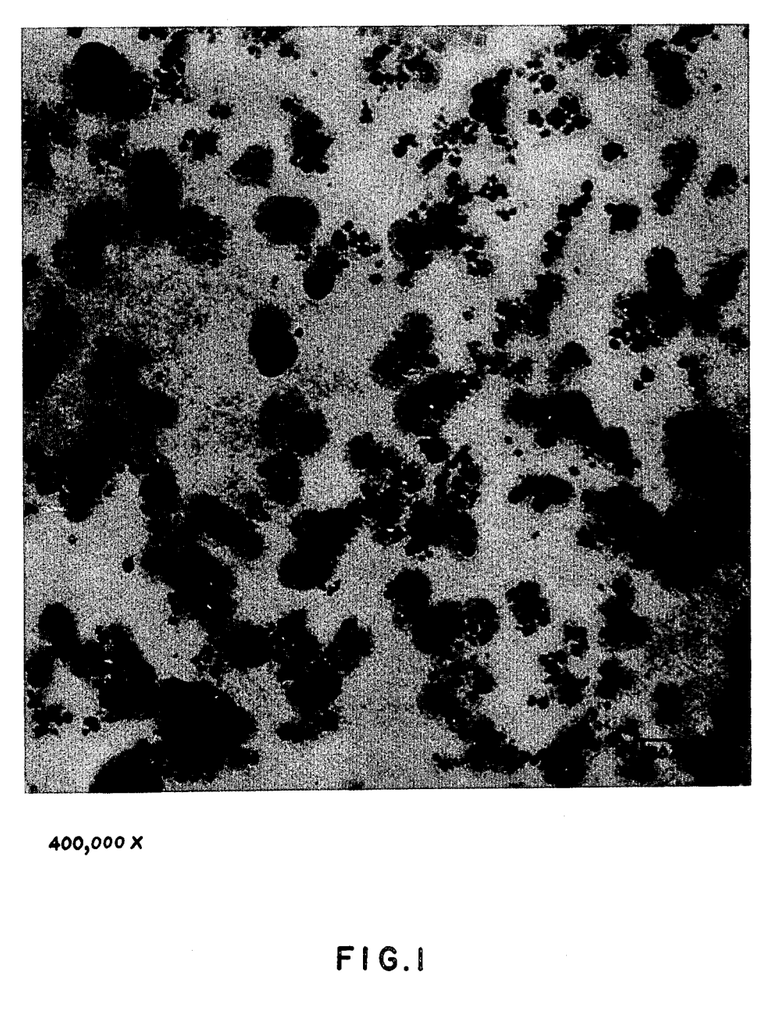
FIG. 1 is an election micrograph illustrating the structure of a magnetic iron compound of the present invention in solution.

The material of FIG. 3c was prepared as a dry solid in the experiment described herein for preparing the material depicted in FIG. 1. The material of FIG. 3d was prepared by adding a solution of 130 ml $H_2O_2$ (nominal 30%) in 4000 ml water to a second solution composed of 682 grams $FeCl_2 \cdot 4H_2O$ and 8000 ml water; as soon as foaming subsided, 1000 ml of $NH_4OH$ (1:1) was added, and the material permitted to stand over night. It was then decanted, re-suspended to 4000 ml with water, allowed to settle, decanted, re-suspended to 2000 ml, filtered, washed with 1000 ml water, re-suspended up to 3000 ml, and again permitted to stand over night. Finally, the cake was oven-dried at 56° C for 2.5 hours, desiccated, ground, re-suspended up to 600 ml, filtered and washed with 200 ml water, and again dried for 2.5 hours at 56° C, desiccated, and ground to pass a screen having 0.105 mm openings.

Comparison of the X-ray diffraction patterns indicates that the characteristic pattern of natural magnetite (FIG. 3b) is possessed by both the freshly precipitated magnetite (FIG. 3d) and by a material according to the invention prepared from freshly precipitated magnetite, tartaric acid and Quadrol (FIG. 3c).

In the Table below, X-ray diffraction line spacings and intensities for the freshly precipitated magnetite and for the magnetitetartrate-Quadrol compound are compared with literature values for $Fe_3O_4$ (magnetite) and for gamma ferric oxide. As noted above, the spacings and intensities for freshly precipitated magnetite correspond closely to those for products of the invention (FIG. 3c) wherein the magnetite has been treated with a hydroxy-carboxylic acid and with a base.

X-RAY SPACINGS AND INTENSITIES
Experimental Data for Freshly Precipitated Magnetite and Magnetite-Tartrate-Quadrol Compound, and Literature Data for Magnetite $Fe_3O_4$
(ASTM Card 11-614) and $Fe_2O_3$ (4-0755 and 15-615)

| Freshly Ppt. Magnetite | | Magnetite-Tartrate -Quadrol Compd. | | magnetite (Lit.) $Fe_3O_4$ | | $Fe_2O_3$ (Lit.) | |
|---|---|---|---|---|---|---|---|
| d(A) | I | d(A) | I | d(A) | Io | d(A) | Io |
| 4.76 | vw | — | — | 4.85 | 40 | 4.82 | 5 |
| 2.93 | mw | 2.934 | mw | 2.966 | 70 | 2.95 | 34 |
| — | — | — | — | — | — | 2.78 | 19 |
| 2.49 | vs | 2.515 | vs | 2.530 | 100 | 2.52 | 100 |
| — | — | — | — | 2.419 | 10 | 2.41 | 1 |
| — | — | — | — | — | — | 2.32 | 6 |
| 2.08 | m | 2.084 | m | 2.096 | 70 | 2.08 | 24 |
| 1.70 | w | — | — | 1.712 | 60 | 1.70 | 12 |
| 1.607 | ms | 1.608 | ms | 1.614 | 85 | 1.61 | 33 |
| 1.476 | s | 1.475 | s | 1.483 | 85 | 1.48 | 53 |
| 1.319 | vvw | — | — | 1.327 | 20 | 1.32 | 7 |
| 1.282 | vw | 1.274 | vw | 1.279 | 30 | 1.27 | 11 |
| — | — | — | — | 1.264 | 10 | 1.26 | 3 |
| 1.205 | vw | — | — | 1.214 | 30 | 1.21 | 5 |
| 1.118 | w | — | — | 1.1214 | 30 | 1.12 | 7 |
| 1.089 | m | 1.093 | m | 1.0922 | 60 | 1.09 | 19 |
| 1.045 | w | 1.044 | w | 1.0489 | 40 | 1.04 | 8 |

Note: Intensity:
w = weak
m = medium
s = strong
v = very

MAGNETIC PROPERTIES

The magnetic properties exhibited by the members of this new class of organo-iron compounds are some of the distinguishing features of these materials. When they have been isolated in the form of dry solids they exhibit a magnetic attractiveness of a magnitude comparable to that shown by magnetite. Some of these dry powders may be solubilized with water to form solutions which possess magnetic properties. Such a solution will exhibit a mass movement to a magnetic field. Thus, the magnetic fluid may be caused to move up the side of a containing vessel in response to a suitable magnetic field. Such a liquid may be caused to assume and to indefinitely hold a position that is opposed to its normal gravitational deportment through the employment of a suitable magnet. When the magnetic field is of sufficient intensity it is possible to cause the appearance of a series protuberances upon the surface of the liquid that is opposed by a magnetic field. There is a relationship between the magnetic field and the number and the size and positioning of these magnetic protuberances, which will appear and change and disappear and later reappear upon the surface of the liquid in response to positional variation of the relationship of the magnetic field to the liquid.

If the liquid is brought within the influence of a magnetic field of a yet higher intensity, it is observed that the magnetized fluid has developed the property of resisting any deformation of its physical arrangement in space by an external force. If, under such influence, the material is stirred with a glass rod or a similar instrument, the material would appear to possess a gel type of property or consistency, combined with a sort of an elasticity that causes the material to immediately return to its original condition when the stirring action is ceased. This resistance to an attempted alteration of its physical disposal by an external force, while it is being acted upon by a strong magnetic field, is proportional to the alignment of the liquid with respect to the magnetic field. With a sufficiently strong magnetic field the magnetic fluid will appear to have been transformed into an almost solid material, because of the interaction between it and the magnetic field of force. The liquid need not be contained in a vessel, but only separated from the magnetic field by some septum such as may be conveniently provided by a sheet of glass. All apparent evidence of these responses and changes in properties disappear immediately upon the removal of the magnetic field without any indication of residual effects.

These magnetic phenomena have not been previously reported, since materials possessing the properties of those covered by this invention had not heretofore been known. Aside from the theoretical importance of this invention is the practical utilization of these materials.

UTILITY

Liquids of the present invention exhibit the properties under the influence of magnetic fields which have been here described and provide many practical applications in various directions. There is utility in mechanical systems wherein a magnetic liquid is incorporated and utilized to perform a function that results from its response to the influence of a magnetic field. There are space-age applications for the use of such a liquid in interstellar space where substantial gravitational fields do not exist, wherein by the proper utilization of magnetic fields movements in magnetic fluids may be effected which can perform functions in the operation of equipment of various kinds. There is practical utility in fluid amplifiers containing magnetic fluids for use as control devices. Such magnetic fluids offer a practical extension of the field of magnetohydrodynamics. In the field of biology it is possible to complex physiologically active materials into soluble magnetic compounds and to inject such fluids into biological systems and to control the movements and the utilization of these agents by means of magnetic fields. Also, numerous children's toys and games can utilize a magnetic fluid as a part of the assembly. It is an entirely new concept for a liquid to possess such magnetic properties as have been here described, consequently this invention opens a new dimension to all operations which utilize fluids.

ELECTRON MICROSCOPY

An exhaustive examination was made by the technique of electron microscopy of samples of intermediates prepared at various stages from numerous experimental runs which correspond to the examples which later appear in this specification. These studies demonstrate that under very high magnifications in the range of 400,000 diameters with equipment possessing a resolution power in the range of 10 A that these materials are relatively uniform in general appearance with ultimate individual particle-sizes in the range of 25 to 50 A. When it is considered that the crystallographic unit cell for magnetite has a dimension a = 8.37 A it is apparent that these small particles cannot contain very many unit cells of magnetite, especially since the organic portions of the molecule must be taken into account.

Referring to the drawings, FIG. 1 illustrates an electron micrograph taken of a solubilized sample of a gelatin-free organo-iron compound (i.e., magnetite tartrate) dissolved in ethylene glycol, the photograph having been taken at a magnification of 400,000 diameters. The particle size may be readily compared to the scale indicator showing 250 A at that magnification. This sample was prepared by admixing 130 ml of nominal 30% hydrogen peroxide in 4000 mm water, with 682 grams $FeCl_2 \cdot 4H_2O$ in 8000 ml water; the two solutions were combined by adding the peroxide solution to the ferrous chloride solution. As soon as foaming subsided, 1000 ml of 1:1 $NH_4OH$ was added, and the resulting solution permitted to stand for four hours, after which an additional 100 ml of the peroxide solution was added. This material was washed twice by decantation with a total of 16 liters water, then suspended in 3400 ml water, and transferred to a five-liter flask. Then, 1000 ml solution containing 250 grams tartaric acid was added, and the mixture heated for 2.5 hours and then filtered, washed with water, and re-suspended and again filtered. Thereafter, the filter cake was re-suspended in 2000 ml solution containing ammonia to a pH of about 8; hydrochloric acid was added to a pH of 2.4 to precipitate the material, which was then filter washed and re-suspended twice. A portion of this was treated with Quadrol to a pH of 8 and then dried.

The above-dried material was dispersed ultrasonically in ethylene glycol, placed on microscope grids and evaporated to dryness. Photomicrographs were then taken.

Figure 2:
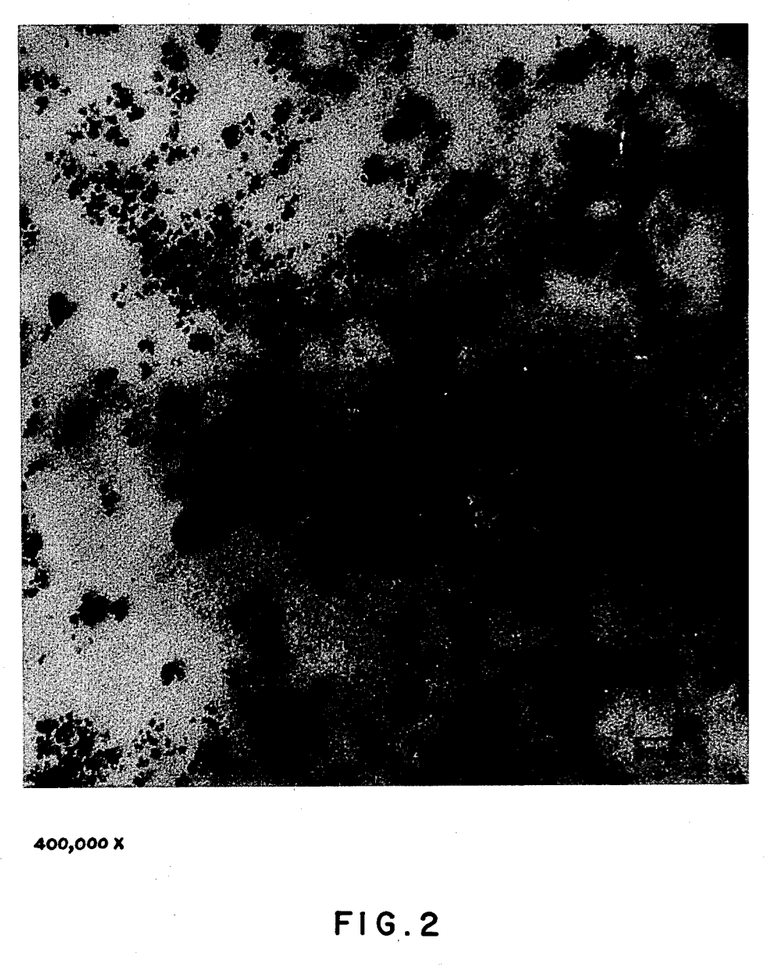
FIG. 2 is an electron micrograph illustrating the structure of another form of magnetic iron compound of the present invention in solution.

FIG. 2 illustrates an electron micrograph of a material prepared in Group B, Example No. 3, which had been treated with Quadrol and thereafter dispersed and prepared as described above in connection with FIG. 1. Magnification is again at 400,000 diameters.

PREFERRED PROCESS FOR PREPARATION

The preferred general process utilized for the preparation of the materials of this invention consists in: A. the preparation of a solution of a protein, such as gelatin, or its degradation products, which products are conveniently obtained by the action of hydrogen peroxide upon the aqueous solution or suspension of the protein under autoclave conditions of heat and pressure; B. adding the above solution, which has been fortified with a sufficient quantity of hydrogen peroxide, to a solution of ferrous chloride which will be oxidized by a predetermined amount of the hydrogen peroxide to a solution containing the proper stoichiometric ratio of ferrous and ferric ions for the preparation of magnetite; C. adding to this mixture, with agitation, a slight excess above the theoretical quantity of ammonium hydroxide required to convert all of the chlorine present in the solution to ammonium chloride, while simultaneously, under in situ reaction conditions, magnetite is being formed, and during the course of its genertion is reacting with the protein and/or its degradation products to produce an insoluble precipitated compound that represents a combination between organic elements and ferromagnetic iron, which material is readily influenced or attracted by a magnetic field, and may be separated by filtration, washing with water and drying for utilization in this form.

The product from C., above, may be further processed in order to obtain valuable derived materials, and in this case the preferred procedure is, D., the suspension of the material above obtained in its original supernatant liquor and the treatment of this material with hydrogen peroxide under ordinary conditions, separating the insoluble material by filtration and washing with water (this treatment with hydrogen peroxide may be omitted and the following processing steps applied to the wet cake obtained from C. above); E., reacting the above obtained wet filter cake with a solution of a hydroxy-carboxylic acid, from which group of acids tartaric acid, and citric acid are suitable examples, utilizing conditions of heat and agitation for effecting the desired chemical reactions, separating the insoluble material by filtration and washing with water; F. reacting the above obtained wet filter cake with an organic base, which possessed a dissociation constant, $K_b$ in excess of about $1 \times 10^{-6}$, from which group of bases piperidine and tetramethylguanidine are suitable examples, which reaction results in the solution of the insoluble material to form a chemical compound which is characterized by its solubility in water and by the presence of iron in the compound in the ferromagnetic state, which is manifested by the property of the material to be influenced and attracted by a magnetic field in the separate states of a dry powder, moist powder and in water solution.

It is possible to make a variation in the processing of the wet filter cake obtained in E., above, that provides an economy in the use of raw materials and which also affords a step of purification, wherein the wet filter cake is dissolved in aqueous ammonia and the ammoniacal solution freed from traces of impurity by filtraton before being precipitated in a titration manner with a dilute acid such as hydrochloric acid or sulphuric acid, thus to obtain a precipitated material that represents some purification and modification of the crude produce from E., above, which material may be filtered and washed with water and then solubilized with a suitable organic base such as piperidine or tetramethylguanidine under titration conditions. This solution may be taken to dryness at low temperature and purified from traces of excess organic base and other soluble impurities by washing with suitable organic solvents such as isopropyl alcohol or methyl alcohol. The dry powder remaining from this treatment possesses the magnetic characteristics described above as well as a high degree of solubility in water. It may be utilized as a dry powder or it may be redissolved in water for use as a magnetic solution.

An analytical amino acid analysis for a typical gelatin utilized in these studies is reproduced below, together with the product resulting from the action of hydrogen peroxide or gelatin following the procedure herein described:

TABLE NO. 1

| Amino Acid Analysis Weight-Percent | | |
|---|---|---|
| | Original Gelatin | Gelatin $H_2O_2$ Treated |
| Alanine | 9.36 | 10.64 |
| Valine | 2.12 | 2.12 |
| Glycine | 22.97 | 25.16 |
| Isoleucine | 1.18 | 1.06 |
| Leucine | 2.97 | 2.80 |
| Proline | 13.11 | 13.14 |
| Threonine | 1.77 | 1.90 |
| Serine | 3.21 | 3.31 |
| Methionine | & trace | & trace |
| Hydroxyproline | & 12.10 | & 12.33 |
| Phenylalanine | 1.95 | 1.70 |
| Aspartic Acid | 6.04 | 6.21 |
| Glutamic Acid | 10.71 | 11.36 |
| Tyrosine | 0.20 | 0.03 |
| Lysine | 3.64 | 3.19 |
| Histidine | 0.91 | 0.73 |
| Arginine | 8.16 | 8.16 |
| Half-cystine | 0.00 | 0.00 |
| | 100.40 | 103.84 |

TABLE NO. 1-continued

| Amino Acid Analysis Weight-Percent | | |
|---|---|---|
| | Original Gelatin | Gelatin $H_2O_2$ Treated |
| Water | 12.74 | 3.77 |

Intermediates from various experimental runs which utilized gelatin degradation products were subjected to amino acid analysis employing the gas-liquid chromatographic procedures which have been developed by Gehrke and co-workers (Charles W. Gehrke, et al., *Quantitative Gas-Liquid Chromatography of Amino Acids in Proteins and Biological Substances*, Library of Congress Catalogue Card Number 68-57507 (1968)).

Below are tabulations of such analyses for intermediate products corresponding to fractions described in the experimental examples of this specification. These results demonstrate the existence of amino acid elaborations in these materials.

TABLE NO. 2

| | Amino Acid Analysis | | | | |
|---|---|---|---|---|---|
| | I | II | III | IV | V |
| Alanine | 0.89 | 0.73 | 0.90 | 0.81 | 1.08 |
| Valine | 0.13 | 0.11 | 0.21 | 0.17 | 0.24 |
| Glycine | 2.35 | 2.11 | 2.40 | 2.20 | 2.45 |
| Isoleucine | 0.05 | 0.03 | 0.13 | 0.11 | 0.15 |
| Leucine | 0.14 | 0.10 | 0.33 | 0.32 | 0.31 |
| Proline | 0.61 | 0.48 | 1.26 | 1.05 | 1.40 |
| Threonine | 0.14 | 0.11 | 0.18 | 0.17 | 0.19 |
| Serine | 0.26 | 0.22 | 0.31 | 0.28 | 0.31 |
| Methionine | & trace | & trace | & trace | & trace | & trace |
| Hydroxyproline | & 0.74 | & 0.59 | & 1.18 | & 1.05 | & 1.30 |
| Phenylalanine | 0.02 | 0.02 | 0.10 | 0.16 | 0.17 |
| Aspartic Acid | 0.86 | 0.78 | 0.64 | 0.60 | 0.57 |
| Glutamic Acid | 1.30 | 1.22 | 1.31 | 1.24 | 1.02 |
| Tyrosine | & trace | 0.00 | 0.00 | 0.00 | & trace |
| Lysine | & 0.21 | 0.20 | 0.33 | 0.30 | & 0.44 |
| Histidine | 0.00 | 0.00 | 0.00 | 0.00 | 0.00 |
| Arginine | 0.02 | 0.02 | 0.03 | 0.05 | 0.23 |
| Half-cystine | 0.00 | 0.00 | 0.00 | 0.00 | 0.00 |
| | 7.72 | 6.73 | 9.31 | 8.51 | 9.86 |
| Water | 2.57 | 3.85 | 1.44 | 2.95 | 1.35 |
| Total | 10.29 | 10.58 | 10.75 | 11.46 | 11.21 |

I Brown magnetic compound Example No. 3 - Stage 3
II Purified red magnetic compound (HCl precipitated) Example No. 3 - Stage 5
III Brown magnetic compound Example No. 5 - Stage 3
IV Purified red magnetic compound (HCl precipitated) Example No. 5 - Stage 5
V Dried filtrate from brown compound Example No. 5 - Stage 3

It appears from this data that the amino acid relationship remains substantially the same in the peptide derived from the gelatin degradation as in the original gelatin.

WORKING EXAMPLES

Experimental details for the preparation of some of the members of this new class of organo-iron compounds is given hereunder in a series of examples which serve to illustrate certain applications of this invention.

Group A of these examples embraces the invention in the simpler form without the involvement of such organic materials as proteins and protein degradation products. Group B of the examples treats with the protein modifications.

GROUP A

EXAMPLE NO. 1

Stage 1 Preparation of magnetite

The magnetite is prepared from ferrous chloride by first oxidizing two-thirds of the iron to the ferric state by the use of hydrogen peroxide. It has been determined that 0.0611 grams of hydrogen peroxide 100% is required for each gram of $FeCl_2 \cdot 4H_2O$ in order to effect this conversion. Since there are some variations in the strength of available solutions of hydrogen peroxide, it is necessary to titrate the concentration of each lot of material when it is used in order to maintain the proper ratio between the reactants. One gram of potassium permanganate is dissolved in water to make 500 ml of solution. Each ml of such potassium permanganate solution is equivalent to 0.001067 grams of hydrogen peroxide 100%. In practice, 1 ml of the aqueous solution of hydrogen peroxide as hereinunder employed, is diluted to 50 ml with water and titrated with the standard potassium permanganate solution to a faint pink end point. With this information necessary adjustments in the quantities of reactants can be made so as to maintain the proper stoichiometric ratios.

616 grams of pure ferrous chloride ($FeCl_2 \cdot 4H_2O$) (containing 173.03 grams of iron) are dissolved in 2000 ml of water. The solution should be a light emerald green color, free from insoluble impurities and neutral to Congo Red test paper.

110 ml of hydrogen peroxide (30% nominal) is diluted with 4000 ml of water and this solution quickly added, with agitation to the solution of ferrous chloride contained in a 12 inches × 12 inches Pyrex jar. There is an immediate evolution of gas accompanied by foaming, which quickly subsides and the color of the solution has turned to a reddish brown. This solution is diluted by the addition of approximately 5000 ml of water and to this agitated solution is quickly added 960 ml of an aqueous solution of ammonium hydroxide, which has been prepared by mixing 480 ml of ammonium hydroxide containing 28–30% free ammonia with an equal volume of water. During the addition of ammonia there is a changing of coloration from reddish brown to a bluish green as the precipitation is completed. This bluish green precipitate is allowed to settle and the color gradually darkens to a black. As it darkens it develops ferromagnetic qualities which may be observed by the movement of the precipitate by a magnet brought to the wall of the containing vessel. A small amount of reddish foam gradually develops as a surface layer.

The magnetite thus formed is not isolated as such, but is subjected to further chemical treatment.

Stage 2—Preparation of brown magnetic compound

After the material from Stage 1 has been allowed to stand for a few hours for the precipitate to completely settle, the supernatant liquid possesses a pH of approximately 9.0. The reddish surface layer of impurity is removed so as not to contaminate the precipitated material, thereafter the precipitated magnetite is suspended in its supernatant liquid by agitation and 200 ml of hydrogen peroxide (30% nominal) is added to the agitated slurry. This addition is accompanied by a rapid evolution of gas which quickly subsides. After waiting about one hour, the material is treated with a second portion of 200 ml of hydrogen peroxide (30% nominal) in the same manner with similar results. During this period of oxidation the precipitate has gradually undergone a change in coloration from a dark black to a deep brown. The brown precipitate is allowed to settle, the bulk of the supernatant liquid is syphoned away so as not to disturb the precipitate, an amount of water equal in quantity to the removed supernatant liquid is then added and the precipitate is agitated with the fresh water to wash it from impurities. The precipitate is allowed to settle and again washed by decantation in the same manner, again allowed to be settled and filtered and washed on the filter with approximately 2000 ml of water. The bulk of soluble impurities are removed by this washing procedure.

This brown compound is also ferromagnetic and contains 65.46% iron.

Stage 3—Preparation of complex

The wet filter cake of brown magnetic compound from Stage 2 is suspended by agitation in 2800 ml of water at about 80° C, transferred to a 5 liter round bottom flask and to this suspension is added a solution of 254 grams of tartaric acid in 800 ml of water that has been heated to about 80° C. Handling usually reduces the fluid temperatures to around 70° C. The reaction vessel is heated with agitation on a water bath for a period of approximately two hours after the internal temperature has been brought to a temperature range of 92°–94° C, filtered hot and the cake washed with approximately 1000 ml of cold water. The cake is suspended in water to make a total volume of approximately 3400 ml, filtered and again washed by suspension and filtered. The red filter cake is still not of the desired purity and it is subjected to a chemical purification step.

The filtrates from this operation had dissolved iron compounds which contained 19.6 grams of iron. This represents a loss of 11.32% of the original iron input on the basis of elemental iron.

Stage 4—Purification of complex

The red magnetic compound obtained in Stage 3 is purified by suspending it with agitation in 500 ml of water and solubilizing it by the addition of 73 ml of ammonium hydroxide containing 28–30% free ammonia. This solution is allowed to stand over night, diluted with water to 4000 ml and precipitated with 2560 ml of hydrochloric acid of a concentration obtained by dissolving 36 ml of hydrochloric acid containing 36.5–38% of hydrogen chloride in water to make 1000 ml of solution. The precipitated red material is filtered, resuspended in water to make a total volume of approximately 3400 ml, filtered and again washed by suspension in the same manner and filtered.

This red compound is also ferromagnetic and contains 55.95% iron in a chemical combination with carbon, hydrogen and oxygen.

The filtrates from this stage contain dissolved iron compounds representing an iron content of 25.9 grams, which amounts to a loss of 14.97% of the original iron input on the basis of elemental iron.

Stage 5—Solubilization of complex

The purified red magnetic compound contained in Stage 4 is converted into a water soluble form by a further reaction which results in the formation of a salt. This may be accomplished by reacting it with any one of a great number of basic materials under conditions which may be chosen to yield a solution of the desired concentration. Piperidine or tetramethylguanidine are very satisfactory materials for this purpose.

The wet filter cake is suspended in 200 ml of water and either 28.4 ml of piperidine or 32.4 ml of tetramethylguanidine gradually added to give in either case a reddish brown solution with a pH in the range of 7.0–7.5. There is a small amount of insoluble material which amounts to 14.8 grams in the case of the piperidine which contains 7.2 grams of iron, representing a loss of 4.16% of the original iron input; and which amounts to 16.2 grams in the case of the tetramethylguanidine which contains 7.9 grams of iron, representing a loss of 4.57% of the original iron input, which may be removed by filtration.

These solutions exhibit the properties of magnetic fluids and may be utilized in this form if desired. They do not represent solutions of pure chemicals, however, and may be purified by a further treatment.

Stage 6—Purification of salts of complex

The solutions of the piperidine and tetramethylguanidine reaction products from the red magnetic compound as prepared in Stage 5 are not completely pure. They are contaminated with small amounts of various materials, including the carbonates, tartrates and other salts of tetramethylguanidine or of piperidine.

These solutions may be purified by a procedure of precipitating the salts from them with a suitable solvent that is water soluble and in which the desired salts have little if any solubility. A convenient solvent is isopropyl alcohol.

In the case of the tetramethylguanidine salt the 200 ml of solution as prepared in Stage 5 is precipitated by pouring it, with stirring, into 800 ml of absolute isopropyl alcohol. The precipitated salt may be conveniently collected at the bottom of the vessel by placing it above the pole of a suitable magnet. The precipitate is washed with an additional 800 ml of absolute isopropyl alcohol, magnetically collected, separated and oven dried at around 55° C.

The yield of tetramethylguanidine salt amounts to approximately 210 grams. This compound contains 56.65% iron, in chemical combination with carbon, nitrogen and oxygen.

In the case of the piperidine salt it is not practical to precipitate it in the same manner as was employed for the tetramethylguanidine salt. To the 200 ml of solution as prepared in Stage 5 is added 100 ml of absolute isopropyl alcohol and this mixture is taken to dryness in an oven at around 55° C. The dry material is twice extracted with 800 ml portions of absolute isopropyl alcohol and the product oven dried at around 55° C.

The yield of piperidine salt amounts to approximately 200 grams. This compound contains 60.15% iron, in chemical combination with carbon, hydrogen, nitrogen and oxygen.

EXAMPLE NO. 2

Stage 1—Preparation of magnetite

The magnetite is prepared by following the usual procedure wherein the following reactants were employed: 595 grams of ferrous chloride (containing 167.14 grams of iron), 110 ml of hydrogen peroxide (30% nominal) and 960 ml of ammonium hydroxide (1:1 with water).

Stage 2—Preparation of brown magnetic compound

This stage was eliminated in this example.

Stage 3—Preparation of complex

The magnetite from Stage 1 was washed in a manner similar to that which is normally employed for the brown magnetic compound, and this washed material is reacted with 254 grams of tartaric acid following the standard procedure.

The compound produced as a result of this reaction was yellowish brown in color rather than a reddish hue, indicating a contamination with a polynuclear yellow-green compound earlier mentioned in the description of this reaction.

The filtrates from this operation had dissolved iron compounds which contained 14.2 grams of iron. This represents a loss of 8.49% of the original iron input.

Stage 4—Purification of complex

The standard procedure was followed. Solubilization was effected by the use of 135.5 ml of ammonium hydroxide (28–30%) and precipitation was attained by the use of 6480 ml of hydrochloric acid of the usual concentration.

The final product was a reddish colored ferromagnetic material that contained 61.06% iron in a chemical combination with carbon, hydrogen and oxygen.

The filtrates contained dissolved iron compounds representing an iron content of 73.6 grams which amounts to a loss of 44.03% of the original iron input.

Stage 5—Solubilization of complex

The standard procedure was followed. The piperidine required amounted to 9.0 ml which is equivalent to 10.4 ml of tetramethylguanidine. The insoluble material amounts to 8.6 grams in the case of the piperidine, which contains approximately 4.3 grams of iron, representing a loss of 2.57% of the original iron input and 3.6 grams in the case of the tetramethylguanidine, which contains approximately 1.8 grams of iron, representing a loss of 1.07% of the original iron input.

Stage 6—Purification of salts of complex

The standard procedure was followed.

The yield of the tetramethylguanidine salt amounts to approximately 122.6 grams. This compound contains 62.80% iron, in chemical combination with carbon, hydrogen, nitrogen and oxygen.

The yield of the piperidine salt amounts to approximately 115.8 grams. This compound contains 64.33% iron, in chemical combination with carbon, hydrogen, nitrogen and oxygen.

EXAMPLE NO. 3

Stage 1—Preparation of magnetite

The magnetite is prepared by following the usual procedure wherein the following reactants were employed: 602 grams of ferrous chloride (containing 169.10 grams of iron), 115 ml of hydrogen peroxide (30% nominal) and 960 ml of ammonium hydroxide (1:1 with water).

Stage 2—Preparation of brown magnetic compound

The brown magnetic compound is prepared in the usual manner.

Stage 3—Preparation of complex

The usual procedure was followed except that 216 grams of citric acid was employed rather than the tartaric acid of other examples.

The filtrates from this operation had dissolved iron compounds which contained 42.7 grams of iron. This represents a loss of 25.25% of the original iron input.

Stage 4—Purification of complex

The standard procedure was followed. Solubilization was effected by the use of 9.0 ml of ammonium hydroxide (28–30%) and precipitation was attained by the use of 380 ml hydrochloric acid of the usual concentration.

The final product was a reddish colored ferromagnetic material that contained 62.94% iron in chemical combination with carbon, hydrogen and oxygen.

The filtrates contained dissolved iron compounds representing an iron content of 0.7 grams which amounts to a loss of 0.41% of the original iron input.

Stage 5—Solubilization of complex

The standard procedure was followed. The piperidine required amounted to 10.4 ml which is equivalent to 15.0 ml of tetramethylguanidine. The insoluble material amounts to 7.36 grams in the case of the piperidine, which contains approximately 3.68 grams of iron, representing a loss of 2.17% of the original iron input, and 4.4 grams in the case of the tetramethylguanidine, which contains approximately 2.2 grams of iron, representing a loss of 1.30% of the original iron input.

Stage 6—Purification of salts of complex
The standard procedure was followed.
The yield of tetramethylguanidine salt amounts to approximately 201 grams. This compound contains 61.20% iron, in chemical combination with carbon, hydrogen, nitrogen and oxygen.
The yield of the piperidine salt amounts to approximately 197 grams. This compound contains 61.62% iron, in chemical combination with carbon, hydrogen, nitrogen and oxygen.

EXAMPLE NO. 4

Stage 1—Preparation of magnetite
The magnetite is prepared by following a modification of the usual procedure wherein a mixture of ferrous and ferric chlorides is used in the theoretical ratio of one atom of ferrous iron to two atoms of ferric iron. The following reactants were employed: 198.8 grams of ferrous chloride (containing 55.84 grams of iron) and dissolved in 3000 ml of water, which solution was mixed with a solution of 540.6 grams of ferric chloride (containing 111.7 grams of iron) and dissolved in 3000 ml of water, and 1240 ml of ammonium hydroxide (1:1 with water).

Stage 2—Preparation of brown magnetic compound
The brown magnetic compound is prepared in the usual manner.

Stage 3—Preparation of complex
The usual procedure was followed employing 254 grams of tartaric acid.
The filtrates from this operation had dissolved iron compounds which contained 26.9 grams of iron. This represents a loss of 16.95% of the original iron input.

Stage 4—Purification of complex
The standard procedure was followed. Solubilization was effected by the use of 100 ml of ammonium hydroxide (28–30%) and precipitation was attained by the use of 3600 ml of hydrochloric acid of the usual concentration.
The final produce was a reddish brown colored ferromagnetic material that contained 60.50% iron in chemical combination with carbon, hydrogen and oxygen.
The filtrates contained dissolved iron compounds representing an iron content of 35.5 grams which amounts to a loss of 21.19% of the original iron input.

Stage 5—Solubilization of complex
The standard procedure was followed. The piperidine required amounted to 18.0 ml which is equivalent to 22.0 ml of tetramethylguanidine. The insoluble material amounts to 3.52 grams in the case of the piperidine, which contains approximately 1.76 grams of iron, representing a loss of 1.0% of the original iron input and 3.72 grams in the case of the tetramethylguanidine, which contains approximately 1.86 grams of iron, representing a loss of 1.11% of the original iron input.

Stage 6—Purification of salts of complex
The standard procedure was followed.
The yield of the tetramethylguanidine salt amounts to approximately 187.8 grams. This compound contains 61.83% iron, in chemical combination with carbon, hydrogen, nitrogen and oxygen.
The yield of the piperidine salt amounts to approximately 176.8 grams. This compound contains 68.96% iron, in chemical combination with carbon, hydrogen, nitrogen and oxygen.

EXAMPLE NO. 5

Stage 1—Preparation of magnetite
The magnetite is prepared by following a modification of the usual procedure wherein a mixture of ferrous and ferric chlorides is used in the theoretical ratio of one atom of ferrous iron to two atoms of ferric iron. The following reactants were employed: 198.8 grams of ferrous chloride (containing 55.84 grams of iron) and dissolved in 3000 ml of water, which solution was mixed with a solution of 540.6 grams of ferric chloride (containing 111.7 grams of iron) and dissolved in 3000 ml of water, and 1240 ml of ammonium hydroxide (1:1 with water).

Stage 2—Preparation of brown magnetic compound
This stage was eliminated.

Stage 3—Preparation of complex
The magnetite from Stage 1 was washed in the manner normally employed for that of the brown magnetic compound and this washed material was reacted with 254 grams of tartaric acid following the usual procedure.
The product of this reaction was yellowish brown in color which was an indication of impurity.
The filtrates from this operation had dissolved iron compounds which contained 11.4 grams of iron. This represents a loss of 6.80% of the original iron input.

Stage 4—Purification of complex
The standard procedure was followed. Solubilization was effected by the use of 120 ml of ammonium hydroxide (28–30%) and precipitation was attained by the use of 6000 ml of hydrochloric acid of the usual concentration.
The final product was a reddish colored ferromagnetic material that contained 62.18% iron in a chemical combination with carbon, hydrogen and oxygen.
The filtrates contained dissolved iron compounds representing an iron content of 58.4 grams, which amounts to a loss of 34.85% of the original iron input.

Stage 5—Solubilization of complex
The standard procedure was followed. The piperidine required amounted to 11.2 ml which is equivalent to 12.4 ml of tetramethylguanidine. The isoluble material amounts to 0.8 grams in the case of the piperidine, which contains approximately 0.4 grams of iron, representing a loss of 0.24% of the original iron input with substantially the same loss involved in the case of the tetramethylguanidine.

Stage 6—Purification of salts of complex
The standard procedure was followed.
The yield of the tetramethylguanidine salt amounts to approximately 157.3 grams. This compound contains 62.46% iron, in chemical combination with carbon, hydrogen, nitrogen and oxygen.
The yield of the piperidine salt amounts to approximately 151.4 grams. This compound contains 64.18% iron, in chemical combination with carbon, hydrogen, nitrogen and oxygen.

EXAMPLE NO. 6

Stage 1—Preparation of magnetite
The magnetite is prepared by following a more severe modification of the usual procedure wherein 88.5 grams of ferrous chloride (containing 24.9 grams of iron) are dissolved in 500 ml of water and this solution combined with a solution of 240 ml grams of ferric chloride (containing 49.6 grams of iron) dissolved in 750 ml of water, and this mixed solution added to a solution of sodium hydroxide, prepared by dissolving 223 grams of sodium hydroxide in 3000 ml of water and holding the caustic solution at the boiling temperature in an 8000 ml Monel beaker. This mixture is boiled for one hour, allowed to cool to room temperature and transferred to a suitable Pyrex jar.

Stage 2—Preparation of brown magnetic compound

The brown magnetic compound is prepared by following the usual procedure but employing two portions of 89 ml each of hydrogen peroxide (30% nominal).

Stage 3—Preparation of complex

The usual procedure was followed employing 112 grams of tartaric acid.

The filtrates from this opertion were dark red in color and had dissolved iron compounds which contained 21.2 grams of iron. This represented a loss of 28.48% of the original iron input.

Stage 4—Purification of complex

The usual procedure was followed. Solubilization was effected by the use of 18 ml of ammonium hydroxide (28–30%) and precipitation was attained by the use of 1300 ml of hydrochloric acid of the usual concentration.

The final product was a reddish colored ferromagnetic material that contained 64.69% iron in a chemical combination with carbon, hydrogen and oxygen.

The filtrates contained dissolved iron compounds representing an iron content of 2.58 grams, which amounts to a loss of 3.46% of the original iron input.

Stage 5—Solubilization of complex

The standard procedure was followed. The piperidine required amounted to 4.0 ml which is equivalent to 6.0 ml of tetramethylguanidine. The insoluble material amounts to 14.4 grams in the case of the piperidine, which contains approximately 7.2 grams of iron, representing a loss of 9.67% of the original iron input and 16.9 grams in the case of the tetramethylguanidine, which contains approximately 8.5 grams of iron, representing a loss of 11.42% of the original iron input.

Stage 6—Purification of salts of complex

The standard procedure was followed.

The yield of the tetramethylguanidine salt amounts to approximately 66 grams. This compound contains 63.58% iron, in chemical combination with carbon, hydrogen, nitrogen and oxygen.

The yield of the piperidine salt amounts to approximately 64 grams. This compound contains 67.79% iron, in chemical combination with carbon, hydrogen, nitrogen and oxygen.

EXAMPLE NO. 7

Stage 1 — Preparation of magnetite

The magnetite is prepared by following a more severe modification of the usual procedure wherein 99.4 grams of ferrous chloride (containing 27.92 grams of iron) are dissolved in 500 ml of water and this solution combined with a solution of 270 grams of ferric chloride (containing 55.78 grams of iron) dissoled in 750 ml of water, and this mixed solution added to a solution of sodium hydroxide, prepared by dissolving 250 grams of sodium hydroxide in 3000 ml of water and holding the caustic solution at the boiling point in an 8000 ml Monel beaker. The mixture is boiled for one hour, allowed to cool to room temperature and transferred to a suitable Pyrex jar.

Stage 2 — Preparation of brown magnetic compound

This stage was eliminated in this example.

Stage 3 — Preparation of complex

The magnetite from Stage 1 was washed in the manner normally employed for that of the brown magnetic compound and this washed material was reacted with 127 grams of tartaric acid following the usual procedure.

The product of this reaction had an olive drab color.

The filtrates from this operation were light yellow in color and had dissolved iron compounds which contained 6.2 grams of iron. This represents a loss of 7.4% of the original iron input.

Stage 4 — Purification of complex

The standard procedure was followed. Solubilization was effected by the use of 55 ml of ammonium hydroxide (28–30%) and precipitation was attained by the use of 2600 ml of hydrochloric acid of the usual concentration.

The final product was a reddish colored ferromagnetic material that contained 67.63% iron in a chemical combination with carbon, hydrogen and oxygen.

The filtrates contained dissolved iron compounds representing an iron content of 31.10 grams, which amounts to a loss of 37.15% of the original iron input.

Stage 5 — Solubilization of complex

The standard procedure was followed. The piperidine required amounted to 6.8 ml which is equivalent to 8.0 ml of tetramethylguanidine. The insoluble material amounts to 15.2 grams in the case of the piperidine, which contains approximately 7.6 grams of iron, representing a loss of 9.08% of the original iron input and 19.0 grams in the case of the tetramethylguanidine, which contains approximately 9.5 grams of iron, representing a loss of 11.35% or the original iron input.

Stage 6 — Purification of salts of complex

The standard procedure was followed.

The yield of the tetramethylguanidine salt amounts to approximately 57 grams. This compound contains 64.76% iron, in chemical combination with carbon, hydrogen, nitrogen and oxygen.

The yield of the piperidine salt amounts to approximately 62 grams. This compound contains 62.99% iron, in chemical combination with carbon, hydrogen, nitrogen and oxygen.

EXAMPLE NO. 8

Stage 1 — Preparation of magnetite

The magnetite is prepared by following the procedure utilized in Example No. 7 with the exception that the solution of sodium hydroxide employed was at room temperature rather than at the boiling point. The mixture was allowed to stand over night.

Stage 2 — Preparation of brown magnetic compound

This stage was eliminated in this example.

Stage 3 — Preparation of complex

The procedure of Example No. 7 was followed.

The product of this reaction had a yellow brown color.

The filtrate from this operation were yellow in color and had dissolved iron compounds which contained 14.9 grams of iron. This represents a loss of 17.80% of the original iron input.

Stage 4 — Purification of complex

The standard procedure was followed. Solubilization was effected by the use of 40 ml of ammonium hydroxide (28–30%) and precipitation was attained by the use of 1600 ml of hydrochloric acid of the usual concentration.

The final product was a reddish colored ferromagnetic material that contained 64.07 iron in a chemical combination with carbon, hydrogen and oxygen.

The filtrates contained dissolved iron compounds representing an iron content of 25.17 grams, which amounts to a loss of 30.07% of the original iron input.

Stage 5 — Solubilization of complex

The standard procedure was followed. The piperidine required amounted to 4.0 ml which is equivalent to 6.0 ml of tetramethylguanidine. The insoluble material amounts to 2.48 grams in the case of the piperidine, which contains approximately 1.24 grams of iron, representing a loss of 1.48% of the original iron input and 2.40 grams in the case of the tetramethylguanidine, which contains approximately 1.20 grams of iron, representing a loss of 1.43% of the original iron input.

Stage 6 — Purification of salts of complex

The standard procedure was followed.

The yield of the tetramethylguanidine salt amounts to approximately 65 grams. This compound contains 65.25% iron, in chemical combination with carbon, hydrogen, nitrogen and oxygen.

The yield of the piperidine salt amounts to approximately 66 grams. This compound contains 64.07% iron, in chemical combination with carbon, hydrogen, nitrogen and oxygen.

EXAMPLE NO. 9

Stage 1 — Preparation of magnetite

The magnetite is prepared by following a modification of the usual procedure wherein a mixture of ferrous and ferric sulphates is used in the theoretical ratio of one atom of ferrous iron to two atoms of ferric iron. The following reactants were employed: 122 grams of ferrous sulphate (containing 24.51 grams of iron) and dissolved in 500 ml of water, which solution was mixed with a solution of 222.9 grams of ferric sulphate (containing 49.01 grams of iron) and dissolved in 4000 ml of water, and 540 ml of ammonium hydroxide (1:1 with water).

Stage 2 — Preparation of brown magnetic compound

The brown magnetic compound was prepared by following the usual procedure but employing two portions of 89 ml each of hydrogen peroxide (30% nominal).

Stage 3 — Preparation of complex

The usual procedure was followed utilizing 121 grams of tartaric acid.

The filtrates from this operation were yellow brown in color and had dissolved iron compounds which contained 5.91 grams of iron. This represents a loss of 8.04% of the original iron input.

Stage 4 — Purification of complex

The standard procedure was followed. Solubilization was effected by the use of 50 ml of ammonium hydroxide (28–30%) and precipitation was attained by the use of 1360 ml of hydrochloric acid of the usual concentration.

The final product was a reddish colored ferromagnetic material that contained 64.07% iron in a chemical combination with carbon, hydrogen and oxygen.

The filtrates contained dissolved iron compounds representing an iron content of 24.86 grams, which amounts to a loss of 33.81% of the original iron input.

Stage 5 — Solubilization of complex

The standard procedure was followed. The piperidine required amounted to 2.2 ml which is equivalent to 2.0 ml of tetramethylguanidine. The insoluble material that separated was small in both instances and was not determined quantitatively.

Stage 6 — Purification of salts of complex

The standard procedure was followed.

The yield of the tetramethylguanidine salt amounts to approximately 64 grams. This compound contains 64.83% iron, in chemical combination with carbon, hydrogen, nitrogen and oxygen.

The yield of the piperidine salt amounts to approximately 66 grams. This compound contains 63.13% iron, in chemical combination with carbon, hydrogen, nitrogen and oxygen.

EXAMPLE NO. 10

Stage 1 — Preparation of magnetite

The magnetite is prepared in exactly the same manner as utilized in Example No. 9.

Stage 2 — Preparation of brown magnetic compound

This stage was eliminated to this example.

Stage 3 — Preparation of complex

The magnetite from Stage 1 was washed in the manner normally employed for that of the brown magnetic compound and this washed material reacted with 121 grams of tartaric acid following the usual procedure.

The product of this reaction was a yellow red in color.

The filtrates from this operation were reddish yellow in color and had dissolved iron compounds which contained 12.56 grams of iron. This represents a loss of 17.08% of the original iron input.

Stage 4 — Purification of complex

The standard procedure was followed. Solubilization was effected by the use of 60 ml of ammonium hydroxide (28–30%) and precipitation was attained by the use of 2200 ml of hydrochloric acid of the usual concentration.

The final product was a reddish colored ferromagnetic material that contained 65.11% iron in a chemical combination with carbon, hydrogen and oxygen.

The filtrates contained dissolved iron compounds representing an iron content of 24.6 grams, which amounts to a loss of 33.46% of the original iron input.

Stage 5 — Solubilization of complex

The standard procedure was followed. The piperidine required amounted to 4.0 ml which is equivalent to 3.8 ml of tetramethylguanidine. The insoluble material that separated was small in both instances and was not determined quantitatively.

Stage 6 — Purification of salts of complex

The standard procedure was followed.

The yield of the tetramethylguanidine salt amounts to approximately 56 grams. This compound contains 63.37% iron, in chemical combination with carbon, hydrogen and oxygen.

The yield of the piperidine salt amounts to approximately 53 grams. This compound contains 66.49% iron, in chemical combination with carbon, hydrogen, nitrogen and oxygen.

EXAMPLE NO. 11

Stage 1 — Preparation of magnetite

The magnetite is prepared by following a modification similar to that employed in Example No. 6 wherein 122 grams of ferrous sulphate (containing 24.51 grams of iron) are dissolved in 500 ml of water and this solution combined with a solution of 222.9 grams of ferric sulphate (containing 49.01 grams of iron) dissolved in 650 ml of water, and this mixed solution added to a solution of sodium hydroxide, prepared by dissolving 250 grams of sodium hydroxide in 3000 ml of water and holding this caustic solution at the boiling temperature in an 8000 ml Monel beaker. This mixture is boiled for one hour, allowed to cool to room temperature and transferred to a suitable Pyrex jar.

Stage 2. Preparation of brown magnetic compound

The brown magnetic compound is prepared by following the usual procedure but employing two portions of 89 ml each of hydrogen peroxide (30% nominal).

Stage 3. —Preparation of complex

The usual procedure was followed utilizing 121 grams of tartaric acid.

The filtrates from this operation were dark red in color and had dissolved iron compounds which contained 26.9 grams of iron. This represents a loss of 36.59% of the original iron input.

Stage 4. —Purification of complex

The standard procedure was followed. Solubilization was effected by the use of 18 ml of ammonium hydroxide (28–30%) and precipitation was attained by the use of 1400 ml of hydrochloric acid of the usual concentration.

The final product was a reddish colored ferromagnetic material that contained 66.44% iron in a chemical combination with carbon, hydrogen and oxygen.

The filtrates contained dissolved iron compounds representing an iron content of 1.7 grams, which amounts to a loss of 2.3% of the original iron input.

Stage 5. —Solubilization of complex

The standard procedure was followed. The piperidine required amounted to 4.6 ml which is equivalent to 6.0 ml of tetramethylguanidine. The insoluble material that separated was small in both instances and was not determined quantitatively.

Stage 6. —Purification of salts of complex

The standard procedure was followed.

The yield of the tetramethylguanidine salt amounts to approximately 65 grams. This compound contains 63.86% iron, in chemical combination with carbon, hydrogen, nitrogen and oxygen.

The yield of the piperidine salt amounts to approximately 64 grams. This compound contains 65.20% iron, in chemical combination with carbon, hydrogen, nitrogen and oxygen.

EXAMPLE NO. 12

Stage 1. —Preparation of magetite

The magnetite is prepared in exactly the same manner as that utilized in Example No. 11.

Stage 2. —Preparation of brown magnetic compound

This stage was eliminated in this example.

Stage 3. —Preparation of complex

The magnetite from Stage 1 was washed in the manner normally employed for that of the brown magnetic compound and this washed material reacted with 121 grams of tartaric acid following the usual procedure.

The product of this reaction was chocolate brown in color.

The filtrates from this operation were of a dark straw color and had dissolved iron compounds which contained 9.18 grams of iron. This represents a loss of 12.48% of the original iron input.

Stage 4. —Purification of complex

The standard procedure was followed. Solubilization was effected by the use of 55 ml of ammonium hydroxide (28–30%) and precipitation was attained by the use of 2400 ml of hydrochloric acid of the usual concentration.

The final product was a reddish colored ferromagnetic material that contained 59.87% iron in a chemical combination with carbon, hydrogen and oxygen.

The filtrates contained dissolved iron compounds representing an iron content of 26.1 grams, which amounts to a loss of 35.50% of the original iron input.

Stage 5. —Solubilization of complex

The standard procedure was followed. The piperidine required amounted to 8.8 ml which is equivalent to 12.8 ml of tetramethylguanidine. The insoluble material that separated was small in both instances and was not determined quantitatively.

Stage 6. —Purification of salts of complex

The standard procedure was followed.

The yield of the tetramethylguanidine salt amounts to approximately 57 grams. This compound contains 61.07% iron, in chemical combination with carbon, hydrogen, nitrogen and oxygen.

The yield of the piperidine salt amounts to approximately 55 grams. This compound contains 62.66% iron, in chemical combination with carbon, hydrogen, nitrogen and oxygen.

EXAMPLE NO. 13

Stage 1—Preparation of magnetite

The magnetite is prepared in exactly the same manner as that utilized in Example No. 11 with the exception that the solution of sodium hydroxide employed was at room temperature rather than at the boiling point. The mixture was allowed to stand over night.

Stage 2—Preparation of brown magnetic compound

This stage was eliminated in this example.

Stage 3—Preparation of complex

The magnetite from Stage 1 was washed in the manner normally employed for that of the brown magnetic compound and this washed material reacted with 121 grams of tartaric acid following the usual procedure.

The product of this reaction was yellow brown in color.

The filtrates from this operation were of a dark straw color and had dissolved iron compounds which contained 13.9 grams of iron. This represents a loss of 18.91% of the original iron input.

Stage 4—Purification of complex

The standard procedure was followed. Solubilization was effected by the use of 50 ml of ammonium hydroxide (28–30%) and precipitation was attained by the use of 1900 ml of hydrochloric acid of the usual concentration.

The final product was a reddish colored ferromagnetic material that contained 62.04% iron in a chemical combination with carbon, hydrogen and oxygen.

The filtrates contained dissolved iron compounds representing an iron content of 22.0 grams, which amounts to a loss of 29.92% of the original iron input.

Stage 5—Solubilization of complex

The standard procedure was followed. The piperidine required amounted to 6.0 ml which is equivalent to 5.6 ml of tetramethylguanidine. The insoluble material that separated was small in both instances and was not determined quantitatively.

Stage 6—Purification of salts of complex

The standard procedure was followed.

The yield of the tetramethylguanidine salt amounts to approximately 55 grams. This compound contains 63.22% iron, in chemical combination with carbon, hydrogen, nitrogen and oxygen.

The yield of the piperidine salt amounts to approximately 52 grams. This compound contains 66.57% iron, in chemical combination with carbon, hydrogen, nitrogen and oxygen.

EXAMPLE NO. 14

Stage 1—Preparation of magnetite

The magnetite is prepared by following the usual procedure wherein the following reactants were employed: 496 grams of ferrous sulphate (containing 99.65 grams of iron) are dissolved in 4000 ml of water and reacted with 70 ml of hydrogen peroxide (30% nominal) dissolved in 2000 ml of water to obtain the proper ratio of ferrous to ferric ions; this solution is precipitated with 533 ml of ammonium hydroxide (1:1 with water).

Stage 2—Preparation of brown magnetic compound

The brown magnetic compound is prepared by following the usual procedure but employing two portions of 124 ml each of hydrogen peroxide (30% nominal).

Stage 3—Preparation of complex

The usual procedure was followed utilizing 140 grams of tartaric acid.

The filtrates from this operation were of a yellowish color and had dissolved iron compounds which contained 7.16 grams of iron. This represents a loss of 7.18% of the original iron input.

Stage 4—Purification of complex

The standard procedure was followed. Solubilization was effected by the use of 60 ml of ammonium hydroxide (28–30%) and precipitation was attained by the use of 2000 ml of hydrochloric acid of the usual concentration.

The final product was a reddish brown colored ferromagnetic material that contained 63.16% iron in a chemical combination with carbon, hydrogen and oxygen.

The filtrates contained dissolved iron compounds representing an iron content of 17.90 grams, which amounts to a loss of 7.18% of the original iron input.

Stage 5—Solubilization of complex

The standard procedure was followed. The piperidine required amounted to 3.8 ml which is equivalent to 4.1 ml of tetramethylguanidine. The insoluble material amounts to 4.9 grams in the case of the piperidine, which contains approximately 2.45 grams of iron, representing a loss of 2.46% of the original iron input and 4.6 grams in the case of the tetramethylguanidine, which contains approximately 2.3 grams of iron, representing a loss of 2.30% of the original iron input.

Stage 6—Purification of salts of complex

The standard procedure was followed.

The yield of the tetramethylguanidine salt amounts to approximately 114 grams. This compound contains 63.09% iron, in chemical combination with carbon, hydrogen, nitrogen and oxygen.

The yield of the piperidine salt amounts to approximately 116 grams. This compound contains 61.87% iron, in chemical combination with carbon, hydrogen, nitrogen and oxygen.

EXAMPLE NO. 15

Stage 1—Preparation of magnetite

The magnetite is prepared by following the usual procedure wherein the following reactants were employed: 517 grams of ferrous sulphate (containing 103.87 grams of iron) are dissolved in 4000 ml of water and reacted with 70 ml of hydrogen peroxide (30% nominal) dissolved in 2000 ml of water to obtain the proper ratio of ferrous to ferric ions; this solution is precipitated with 566 ml of ammonium hydroxide (1:1 with water).

Stage 2—Preparation of brown magnetic compound

This stage was eliminated from this example.

Stage 3—Preparation of complex

The magnetite from Stage 1 was washed in the manner normally employed for that of the brown magnetic compound and this washed material reacted with 151 grams of tartaric acid following the usual procedure.

The filtrates from this operation were of a yellowish color and had dissolved iron compounds which contained 11.04 grams of iron. This represents a loss of 10.63% of the original iron input.

Stage 4—Purification of complex

The standard procedure was followed. Solubilization was effected by the use of 70 ml of ammonium hydroxide (28–30%) and precipitation was attained by the use of 2000 ml of hydrochloric acid of the usual concentration.

The final product was a reddish brown colored ferromagnetic material that contained 62.60% iron in a chemical combination with carbon, hydrogen and oxygen.

The filtrates contained dissolved iron compounds representing an iron content of 29.60 grams, which amounts to a loss of 28.50% of the original iron input.

Stage 5—Solubilization of complex

The standard procedure was followed. The piperidine required amounted to 2.8 ml which is equivalent to 2.4 ml of tetramethylguanidine. The insoluble material amounts to 5.4 grams in the case of the piperidine, which contains approximately 2.7 grams of iron, representing a loss of 2.59% of the original iron input and 5.2 grams in the case of the tetramethylguanidine, which contains approximately 2.6 grams of iron, representing a loss of 2.50% of the original iron input.

Stage 6—Purification of salts of complex

The standard procedure was followed.

The yield of the tetramethylguanidine salt amounts to approximately 92 grams. This compound contains 65.34% iron, in chemical combination with carbon, hydrogen, nitrogen and oxygen.

The yield of the piperidine salt amounts to approximately 91 grams. This compound contains 65.85% iron, in chemical combination with carbon, hydrogen, nitrogen and oxygen.

GROUP B

EXAMPLE NO. 1

Stage 1—Protein Degradation 33.66 grams of gelatin of U.S.P. grade, is suspended in 500 ml of water for one hour, then autoclaved for 10 minutes at 15 pounds steam pressure at 120° C. The solution of gelatin is allowed to cool to room temperature. It has a pH of approximately 4.9, and is a slightly viscous liquid with a light straw color.

20 ml of 30% hydrogen peroxide is now added to the agitated solution of gelatin and the mixture is allowed to stand for one hour at room temperature, then autoclaved for 30 minutes at 15 pounds steam pressure at 120° C. The cooled oxidized solution possesses a slightly lighter straw color than before and has a pH of approximately 3.85. This oxidation has destroyed the gelling properties of the gelatin at this concentration for ordinary temperatures.

The solution of oxidized gelatin which contains free peroxide, as evidenced by the decolorization of lead sulphide test paper, is filtered and diluted to 1000 ml. The peroxide content is adjusted by the addition of fresh hydrogen peroxide so that it shall contain the equivalent of 4.488 grams of hydrogen peroxide as determined by titration with standard potassium permanganate solution.

Stage 2 — Black Magnetic Compound 73.45 grams of pure ferrous chloride ($FeCl_2.4H_2O$) are dissolved in 500 ml of water. The solution should be of light, emerald green color, free from insoluble impurities and neutral to Congo Red test paper. The oxidized gelatin, prepared in Stage 1, is slowly added to the agitated solution of ferrous chloride. The mixture is diluted with 500 ml of water. This solution possesses a reddish brown color and has a pH of approximately 2.75.

60 ml of ammonium hydroxide containing 28–30% free ammonia is diluted to 120 ml and this diluted solution is added to the agitated mixture of oxidized protein and ferrous chloride. During the addition of the ammonia there is a changing of coloration from reddish brown to a bluish green as the precipitation is completed. This bluish green precipitate is allowed to settle and gradually darkens to a deep greenish black. A small amount of reddish foam forms as a surface layer.

After standing over night the supernatant liquid has a pH of approximately 9.0 and from it the precipitated material is removed in such a manner so as not to be contaminated by the red surface layer of impurity and washed with water until it is free from soluble salts, then filtered by any convenient procedure.

The wet filter cake usually weighs in the range of 160–250 grams corresponding to approximately 45 grams of dry material.

This black magnetic precipitate contains approximately 45–48% iron, depending upon various details of preparation. The iron is in chemical combination with the elements carbon, hydrogen, oxygen and nitrogen.

Stage 3 — Brown Magnetic Compound

For the preparation of the brown magnetic compound it is not necessary to have washed and filtered the black magnetic compound but only to have separated it from the surface contamination.

The black magnetic compound and its supernatant liquid are transferred to a vessel having a capacity of from 12 to 15 liters and to it is added with stirring 60 ml of 30% hydrogen peroxide. A considerable gas evolution results and the mixture is lightly stirred until the foamy condition has subsided.

During this oxidation the material gradually changes from black to a deep brownish color. The mixture is allowed to stand for a few hours, whereafter the brown compound is purified by repeated washings with water.

The wet cake obtained by filtration usually weighs in the range of 234 grams corresponding to approximately 41 grams of dry material.

This brown magnetic compound contains approximately 50% iron. The iron is in chemical combination with the elements carbon, hydrogen, oxygen and nitrogen.

Stage 4 — Red Magnetic Compound

The wet filter cake of brown magnetic compound from Stage 3 is suspended in 600 ml of water and to this is added 40 grams of tartaric acid made up to 120 ml of solution and this mixture is heated with agitation of a water bath to a temperature of around 75°–85° C for a period of 90 minutes.

The brown suspension gradually assumes a reddish hue as the reaction progresses. The reaction mixture is cooled and the precipitated material is separated from the supernatant acidic solution and washed repeatedly with cold water. A convenient procedure for the washing of these magnetic materials involves a process of decantation wherein a strong magnetic field is utilized for fixing the magnetic material while the washings are removed.

The wet cake obtained by filtration usually weighs in the range of 160 grams corresponding to approximately 40 grams of dry material.

This red magnetic compound contains approximately 37% iron. The iron is in chemical combination with the elements carbon, hydrogen, oxygen and nitrogen.

Stage 5 — Solubilization of Red Magnetic Compound

The red magnetic compound obtained in Stage 4 is converted into a water soluble form by the preparation of a suitable salt. This may be accomplished by reacting it with any one of a great number of basic materials under conditions which may be chosen to form a solution of the desired concentration. Piperidine or tetramethylguanidine are very satisfactory for this solubilization.

An aqueous slurry may be made of the filter cake and the desired alkali added with stirring in a titration procedure until solution is complete and the resulting solution possesses a pH in the range of 7 or a little higher. The solution may then be filtered to remove traces of impurity.

It is possible to achieve a purification of the solubilized complex prepared by this procedure by treating the solution with an acid such as hydrochloric or sulphuric, under titration conditions, to precipitate a purified version of the material that had been prepared in Stage 4. This purified material may be resolubilized in a similar manner to the procedure above employed and the process can be repeated, if necessary, for a number of times. To achieve an economy in raw materials it is a convenience to utilize ammonia for the first solubilization and tetramethylguanidine or piperidine for purification steps.

The purified solution above obtained may be taken to dryness, preferably at a low temperature, and purified from traces of excess organic base and other soluble impurities by washing with suitable organic solvents which include isopropyl alcohol and methyl alcohol. The dry powder remaining from this purification possesses the magnetic characteristics described earlier and has a very high degree of solubility in water as well as in aqueous glycerol and propylene and ethylene glycols. It may be easily redissolved in water.

The purified compound as prepared by the utilization of piperidine as an organic base contains approximately 54% iron. This iron is in chemical combination with the elements carbon, hydrogen, oxygen and nitrogen.

EXAMPLE NO. 2

Stage 1 — Protein Degradation

The procedure followed is identical with that given in Example No. 1, Stage 1.

Stage 2 — Black Magnetic Compound

The procedure followed is identical with that given in Example No. 1, Stage 2.

Stage 3—Basic Solubilization of Black Magnetic Compound

The processing of the black magnetic compound in Stage 2 of Example No. 1 is completed through the preparation of the washed, wet filter cake. This material may be converted into a water soluble form by the preparation of a suitable derivative. This may be accomplished by reacting it with any one of a great number of basic materials, under conditions which may be chosen to form a solution of the desired concentration. Piperidine and tetramethylguanidine are frequently materials of choice.

Generally speaking, the solubilized materials resulting from this procedure are not as stable as those obtained by following the processing of Example No. 1.

EXAMPLE NO. 3

Stage 1—Protein degradation 89.2 grams of gelatin of U.S.P. grade are suspended in 2000 ml of water, then autoclaved for 10 minutes at 15 pounds steam pressure at 120° C. To the cooled solution, 53.2 ml of 30% hydrogen peroxide is added and the mixture is autoclaved for 30 minutes at 15 pounds steam pressure at 120°C.

Stage 2—Black magnetic compound 607 grams $FeCl_2 \cdot 4H_2O$ are dissolved in 8000 ml water. The oxidized gelatin solution is diluted to 4000 ml and additional hydrogen peroxide is added in sufficient quantity to convert two thirds of the ferrous iron to the ferric state. The oxidized gelatin, hydrogen peroxide solution is added to the ferrous chloride solution and this mixture is treated with 1000 ml of $NH_4OH$ 1:1 dilution. A black magnetic precipitate is formed.

Stage. 3—Brown magnetic compound

The black magnetic precipitated material is allowed to stand approximately for four hours then it is resuspended and treated with 100 ml 30% hydrogen peroxide. During this oxidation the material changes from a black to a deep brownish color. The brown magnetic compound is filtered and washed and the washed material contains approximately 56% iron.

Stage 4—Red magnetic compound

The wet filter cake is suspended up to 3400 ml with water and is combined with 250 grams tartaric in 800 ml of water. This mixture is heated with agitation for two and one half hours at 70°–90° C.

The insoluble magnetic material is filtered and washed and contains approximately 38.1% iron.

Stage 5—Solubilization of red magnetic compound

An aqueous slurry is made of the red magnetic compound and is treated with $NH_4OH$ to a pH of 8.5 to form a solution.

It is possible to achieve a purification of the solubilized complex prepared by this procedure by treating the solution with an acid such as hydrochloric or sulfuric, under titration conditions, to precipitate a purified version of the material that had been prepared in Stage 4. The precipitated complex has an iron content of 50.5%.

The acid precipitated iron complex may be solubilized with a reacting base such as tetramethylguanidine, piperidine and Quadrol.

EXAMPLE NO. 4

Stage 1—Protein degradation 89.2 grams of gelatin of U.S.P. grade are suspended in 1330 ml water, then autoclaved for 10 minutes at 15 pounds steam pressure at 120° C. To the cooled solution 26.6 ml dilute HCl (36% concentrated HCl diluted 1:1 with water) is added and the mixture is autoclaved for 30 minutes at 15 pounds steam pressure at 120° C.

Stage 2—Black magnetic compound

The HCl gelatin solution is diluted to 4000 ml and is added to a combined solution of 800 ml containing 202.3 grams $FeCl_2 \cdot 4H_2O$ and 550 grams $FeCl_3 \cdot 6H_2O$. The above mixture is treated with 1200 ml $NH_4OH$ 1:1 dilution. A black magnetic precipitate is formed.

Stage 3—Brown magnetic compound

The procedure followed is identical with that given in Example No. 3, Stage 3.

Stage 4—Red magnetic compound

The procedure followed is identical with that given in Example No. 3, Stage 4.

Stage 5—Solubilization of red magnetic compound

The procedure followed is identical with that given in Example No. 3, Stage 5.

EXAMPLE NO. 5

Stage 1—Protein degradation 89.2 grams of gelatin of U.S.P. grade are suspended in 1330 ml water, then autoclaved for 10 minutes at 15 pounds steam pressure at 120° C. To the cooled solution, 13.3 ml dilute HCl (36% concentrated HCl diluted 1:1 with water) is added and the mixture is autoclaved for 30 minutes at 15 pounds steam pressure at 120° C.

Stage 2—Black magnetic compound
Stage 3—Brown magnetic compound
Stage 4—Red magnetic compound
Stage 5—Solubilization of red magnetic compound The procedure followed is identical with that given in Example No. 3, Stages 2–5.

EXAMPLE NO. 6

Stage 1—Protein degradation 89.2 grams of gelatin of U.S.P. grade are suspended in 1330 ml $H_2O$, then autolcaved for ten minutes at 15 pounds steam pressure at 120°. To the cooled solution 13.3 ml dilute HCl (36° concentrated HCl diluted 1:1 with $H_2O$) is added and the mixture is autoclaved for fifteen minutes at 15 pounds steam pressure at 120° C.

The procedures followed in Stages 2, 3, 4 and 5 are identical with those given in Example No. 3, Stages 2–5.

EXAMPLE NO. 7

Stage 1—Protein degradation 89 grams $\eta$Proline dissolved in 4000 ml $H_2O$.

Stage 2—Black magnetic compound

The $\eta$Proline solution is added to a combined solution of 8000 ml containing 202.3 grams $FeCl_2 \cdot 4H_2O$ and 550 grams $FeCl_3 \cdot 6H_2O$. The above mixture is treated with 1200 ml $NH_4OH$ 1:1 dilution. A black magnetic precipitate is formed.

Stages 3, 4, 5 are identical in procedure with Example No. 3, Stages 3, 4, and 5.

EXAMPLE NO. 8

Stage 1

89 grams hydroxy Proline dissolved in 4000 ml $H_2O$.

Stages 2, 3, 4, and 5 are identical in procedure with Example No. 7, Stages 2, 3, 4, and 5.

TABLE NO. 3

| | Analytical Comparisons | | | | |
|---|---|---|---|---|---|
| | 4 | 5 | 6 | 7 | 8 |
| Brown Compound | | | | | |
| % Ash | 89.6 | 85.5 | 84.87 | 94.0 | 92.1 |
| % Fe | 64.82 | 59.7 | 61.28 | 65.7 | 64.4 |
| Tartrate Complex | | | | | |
| % Ash | 60.08 | 61.1 | 63.1 | 66.0 | 60.0 |
| % Fe | 42.0 | 42.7 | 44.1 | 46.1 | 41.9 |
| HCl wash ppt. | | | | | |
| % Ash | 80.3 | 76.9 | 77.4 | 86.4 | 77.6 |
| % Fe | 56.14 | 53.7 | 54.1 | 60.4 | 56.1 |
| TMG (Dried) | | | | | |
| % Ash | 70.3 | 68.6 | 70.0 | 75.3 | 68 |
| % Fe | 50.8 | 47.9 | 50.6 | 54.48 | 47.5 |
| Quadrol (Dried) | | | | | |
| % Ash | 62.3 | 62.4 | 63.5 | 65.3 | 57.8 |
| % Fe | 43.5 | 43.6 | 44.4 | 46.2 | 40.4 |

The following is claimed as invention:

1. A process for preparing a water soluble organo-iron compound exhibiting strongly ferromagnetic properties both in the dry state and in aqueous solution, including the steps which comprise:
  a. combining ferrous and ferric ions in approximately the stoichiometric ratio of one molar part ferrous to two of ferric in an alkaline solution to form a precipitate in situ, said precipitate (after drying) having an X-ray diffraction pattern essentially the same as that of magnetite,
  b. reacting the preciptitate with a hydroxy-carboxylic acid to form an alkali-soluble complex, said reaction being effected under conditions to preserve the magnetite-like crystalline structure, and
  c. solubilizing said complex with an alkaline material.

2. Process of claim 1 wherein said stoichiometric ratio is provided by admixing a ferrous salt with a predetermined amount of hydrogen peroxide.

3. Process of claim 1 wherein said precipitation is effected in presence of a member of the group consisting of polypeptides, peptides, amino acids, hydrogen peroxide degraded gelatin, and acid degraded gelatin.

4. Process of claim 3 wherein said member is a hydrogen peroxide-gelatin degradation product.

5. Process of claim 1 wherein said alkaline solution of step (a) comprises ammonium hydroxide.

6. Process of claim 1 wherein said in situ prepared precipitate is treated with hydrogen peroxide to oxidize said ferrous to ferric prior to reaction with said acid.

7. Process of claim 1 wherein said hydroxy-carboxylic acid is employed in sufficient excess to provide said precipitate with acidic groups.

8. Process of claim 1 wherein said hydroxy-carboxylic acid is selected from the group consisting of hydroxy-polycarboxylic acids, polyhydroxy-carboxylic acids, and polyhydroxy-polycarboxylic acids.

9. Process of claim 8 wherein said hydroxy-carboxylic acid is tartaric acid.

10. Process of claim 8 wherein said hydroxy-carboxylic acid is citric acid.

11. Process of claim 1 wherein said alkaline material of step (c) is an organic base having a dissociation constant in excess of about $1 \times 10^{-6}$.

12. Process of claim 11 wherein said base is piperidine.

13. Process of claim 11 wherein said base is tetramethylguanidine.

14. Process of claim 11 wherein said base is 1, 1', 1'', 1''' (ethylenedinitrile)-tetra-2-propanol.

15. A water soluble organo-iron composition exhibiting strongly ferromagnetic properties both in the dry state and in aqueous solution, comprising a material (a) precipitated in situ from an alkaline solution of ferrous and ferric ions in approximately the stoichiometric ratio of one molar part ferrous to two of ferric, (b) complexed with a hydroxy-carboxylic acid to form an alkali-soluble complex, said complexing being effected under conditions to preserve the magnetite-like crystalline structure, and (c) thereafter solublized with an alkaline material, said composition having a magnetite-like crystalline structure as determined by X-ray diffraction.

16. Composition of claim 15 wherein said alkaline material of step (c) is an organic base having a dissociation constant in excess of about $1 \times 10^{-6}$.

17. Composition of claim 15 in which said in situ prepared precipitate is treated to oxidize said ferrous to ferric prior to said complexing with said acid.

18. Composition of claim 15 wherein said complex contains a member of the group consisting of polypeptides, peptides, amino acids, hydrogen peroxide degraded gelatin, and acid degraded gelatin.

19. Composition of claim 15 wherein said complex is free of proteins and protein degradation products.

20. An organo-iron complex from a precipitated magnetite and a hydroxy-carboxylic acid, characterized by:
  a. having a crystalline structure exhibiting an X-ray diffraction pattern essentially the same as that shown in FIG. 3(c),
  b. consisting of from about 25% to about 69% iron, by chemical analysis, on a dry basis,
  c. soluble in water and alkali, and insoluble in acid, and
  d. exhibiting strongly ferromagnetic properties in the dry state and in aqueous solution.

21. A process for preparing a water-soluble organo-iron complex exhibiting strongly ferromagnetic properties both in the dry state and in aqueous solution, comprising:
  a. combining ferrous and ferric ions in approximately the stoichiometric ratio of one molar part ferrous to two of ferric in an alkaline solution to form a precipitate in situ, said precipitate (after drying) having an X-ray diffraction pattern essentially the same as that of magnetite,
  b. reacting the precipitate with a hydroxy-carboxylic acid to form an alkali-soluble complex, said reaction being effected under conditions to preserve the magnetite-like crystalline structure,
  c. and reacting the product step (b) with an organic base having a $K_b$ in excess of about $1 \times 10^{-6}$ to form said water-soluble ferromagnetic compound, said compound likewise having a magnetitie-like crystalline structure by X-ray diffraction.

* * * * *